United States Patent [19]

Weitz et al.

[11] 4,122,285

[45] Oct. 24, 1978

[54] MANUFACTURE OF BUTENEDIOL DIACETATE

[75] Inventors: Hans-Martin Weitz, Bad Durkheim; Ludwig Vogel, Frankenthal; Juergen Hartig, Ludwigshafen; Eckhard Hetzel, Frankenthal, all of Fed. Rep. of Germany

[73] Assignee: BASF Aktiengesellschaft, Ludwigshafen, Fed. Rep. of Germany

[21] Appl. No.: 714,003

[22] Filed: Aug. 13, 1976

[30] Foreign Application Priority Data

Sep. 26, 1975 [DE] Fed. Rep. of Germany ....... 2542925

[51] Int. Cl.$^2$ .............................................. C07C 67/05
[52] U.S. Cl. .................................................... 560/244

[58] Field of Search .................... 260/497 A; 560/244

[56] References Cited

U.S. PATENT DOCUMENTS

| 3,872,163 | 3/1975 | Shimizu | 260/497 A |
| 3,922,300 | 11/1975 | Onoda | 260/497 A |
| 3,959,352 | 5/1976 | Onoda | 260/497 A |

*Primary Examiner*—James O. Thomas, Jr.
*Assistant Examiner*—Michael Shippen
*Attorney, Agent, or Firm*—Keil, Thompson & Shurtleff

[57] ABSTRACT

Butenediol diacetate is manufactured by reaction of butadiene, oxygen and acetic acid over a palladium or platinum catalyst, only liquid, and no gases, being present in the reaction chamber.

7 Claims, 1 Drawing Figure

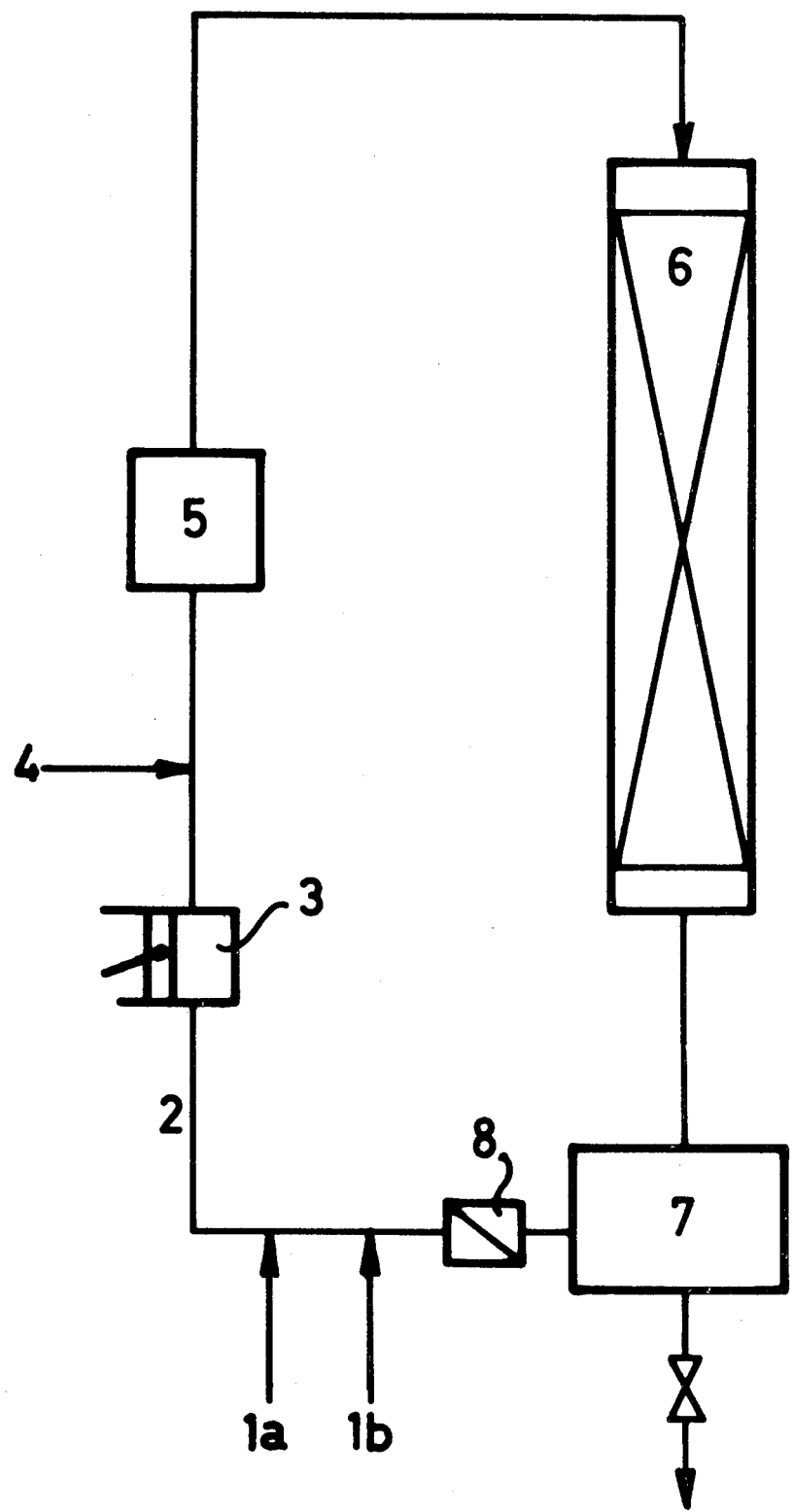

MANUFACTURE OF BUTENEDIOL DIACETATE

The present invention relates to a process for the manufacture of but-1-ene-3,4-diol diacetate and/or but-2-ene-1,4-diol diacetate by reacting butadiene with oxygen and acetic acid in a fluid phase over a solid catalyst, which contains palladium and/or platinum, as well as tellurium and/or antimony.

The reaction of butadiene with oxygen in fluid acetic acid in the presence of solid catalysts containing palladium, to give butenediol diacetate, is disclosed in German laid-open application No. 2,217,452; in this reaction, butadiene and oxygen are also present as gases. The reaction of butadiene with oxygen and acetic acid in the gas phase over palladium-containing catalysts which contain alkali metal salts as promoters is disclosed in German laid-open application DOS No. 2,200,124. A disadvantage of the first-mentioned process is the low rate of reaction. Experience has shown that in the reaction previously known to take place in the gas phase undesirable by-products, e.g., 1-acetoxy-1,3-butadiene are formed, and the reaction must be carried out at low butadiene concentration so that the activity of the catalyst does not suffer.

A disadvantage of all process variants of the prior art, in which oxygen is reacted with butadiene, is that explosive gas mixtures are formed, especially in the event of a fault, i.e., if, for any reason, the conversion should drop.

We have found that the process referred to at the outset can be carried out with high selectivity and very high space-time yield, safely and without formation of undesirable by-products, if the reaction is carried out in the absence of a gas phase, over a catalyst which may or may not be fixed.

Accordingly, the invention relates to an improvement in the process described at the outset, wherein the catalyst is subjected to an amount of liquid such that the latter suffices at all times completely to dissolve the amount of gas fed to the catalyst. This ensures safe operating conditions.

Industrially, the formation of a gas phase in the reaction chamber can be avoided reliably by the following measures:

1. operating under pressure,
2. dissolving the oxygen, as rapidly as possible, in the liquid in a mixing apparatus separate from the reaction chamber and, if necessary,
3. using a reaction chamber which automatically discharges any gases which may be formed.

Suitable conventional apparatus can be employed for admixture of the gases — which may or may not comprise butadiene, but in every case comprise oxygen — to the reaction liquid; for example an ejector, or a flow tube filled with a material having a large surface area, may be used. The maximum amount of oxygen which can be dissolved in the reaction solution under the operating conditions is determined by the solubility coefficient.

To give an indication of the practical effect of the invention, the solubility of oxygen and butadiene in acetic acid and but-2-ene-1,4-diol diacetate at various temperatures is given below. Of course, all the constituents of the reaction mixture mutually affect their solubility, so that data applicable to every conceivable case cannot be given.

TABLE 1 solubility of oxygen in acetic acid/butenediol diacetate $$a = \frac{cm^3 \text{ of } O_2 \text{ (S.T.P.)}}{\text{gram of product} \cdot \text{bar}}$$

| Temperature (° C) | Acetic acid | BEDA* | BEDA-I | BEDA-II* |
|---|---|---|---|---|
| 20 | — | 0.089 | — | 0.089 |
| 25 | 0.190 | — | 0.155 | — |
| 40 | — | 0.098 | — | 0.098 |
| 60 | — | 0.102 | — | 0.102 |
| 100 | 0.186 | — | 0.156 | — |

*pure trans-but-2-ene-1,4-diol diacetate
**mixture of 87% of acetic acid, 10% of trans-but-2-ene-1,4-diol diacetate and 3% of water
***mixture of 28% of but-1-ene-3,4-diol diacetate, 36% of cis-but-2-ene-1,4-diol diacetate and 36% of trans-but-2-ene-1,4-diol diacetate

TABLE 2

Solubility of gaseous butadiene in acetic acid (A) or acetic acid containing 10% of water (B) under a partial pressure of the gas of 1,000 mbar $\left[\frac{cm^3 \text{(S.T.P.)}}{ml}\right]$

| Temperature | A | B |
|---|---|---|
| 20 | 69.9 | 29.6 |
| 40 | 32.0 | 15.0 |
| 60 | 16.8 | 9.0 |
| 70 | 13.3 | 7.1 |

Note: Liquid butadiene is miscible with acetic acid in all proportions at room temperature and at the conventional operating pressure of the process (from 5 to 50 bars).

The reaction yields and space-time yields achievable by means of the invention, on the basis of the above quantitative data, may be seen from the Examples to be discussed later.

The FIGURE shows a possible reaction scheme.

The reactor consists of a 4 m long jacketed steel tube of internal diameter 20 mm. The reaction temperature is controlled by regulating the flow of steam through the outer jacket.

The starting materials may be fed in either at the top or at the bottom. The schematic drawing appended shows the embodiment where they are fed in at the top.

Acetic acid and liquid butadiene are introduced into the reaction system from separate reservoirs by means of pumps, via the product lines 1a, 1b. To prevent the raw materials flowing directly into the separator 7 a non-return valve 8 is provided between 1 and 7. The liquid starting mixture is fed to the suction side of the pump 3 through the product line 2. The gaseous oxygen via 4 is fed in on the pressure side of the pump 3. The mixing apparatus 5, which ensures that the oxygen introduced dissolves completely in the starting mixture, consists of a long packed tube. In order to check whether the oxygen has dissolved completely, a sight glass and control means are provided downstream from the mixing apparatus and permit gaseous materials to be separated off by conventional methods.

The product mixture issuing from the reactor enters a buffer vessel (separator) 7; the discharge therefrom is controlled by a pressure regulator. A part of the product discharged can, if appropriate, be recycled.

Of course, a horizontal reactor can also be used. However, it is particularly advantageous to operate the vertical reactor, described above, in an upward direction. In that case it may be necessary to provide mechanical means to ensure that the catalyst charge does not float. Of course, the shape of the reactor is not restricted to a more or less compact tower and instead the reactor may consist, for example, of a tubular loop or coil. Though continuous operation has advantages, the reaction can also be carried out batchwise in the conventional apparatuses.

The reaction temperature is in general from 60° to 120° C. and preferably from 70° to 110° C. Whilst temperatures below 60° C. are also possible in principle, the space-time yield drops rapidly. Equally, temperatures above 120° C. are possible but the formation of by-products increases.

Depending on the procedure followed, the reaction pressure is in general from atmospheric pressure to about 300 bars, a pressure of from 5 to 50 bars being preferred.

The conventional processes of manufacture of supported metal catalysts may be used for the manufacture of the catalysts used in the process.

The catalyst can be manufactured, for example, by introducing a carrier into a solution, or successively into a plurality of solutions, which has or have been obtained by dissolving the palladium, platinum, tellurium and/or antimony compound in a suitable solvent; the solvent is then distilled off in order to deposit the active component on the carrier, and the catalyst thus prepared is reduced in a stream of hydrogen or by means of a reducing compound, eg. hydrazine, methanol or formaldehyde.

The catalyst can also be manufactured by suspending the carrier in a suitable solution of the active components, precipitating the components in a suitable manner and then reducing them.

Further, a catalyst can be manufactured by applying the components onto the carrier from a solution simultaneously with a reducing agent, eg. hydrazine.

As indicated above, the components may be deposited on the carrier either simultaneously or successively.

The palladium compound used to manufacture the catalyst is not a particularly decisive factor though, for cost reasons, a halogen-containing palladium compound, eg. palladium chloride or sodium palladium chloride, is used advantageously. However, it is of course also possible to use other palladium compounds, eg. sodium palladium sulfate, palladium acetate, palladium nitrate and palladium oxide.

There is also no particular restriction regarding the platinum compound used to manufacture the catalyst. For example, platinum chloride, platinum acetate, platinum nitrate, platinum oxide and other platinum compounds, eg. hexachloroplatinic acid or sodium platinum sulfate, may be used.

Palladium and platinum are active as catalysts either individually or as a mixture. The other components used to manufacture the catalyst are tellurium and/or antimony; their nitrates, halides, sulfates, oxides or other similar compounds may be used to manufacture a catalyst of high activity.

As a rule, the concentration of palladium and/or platinum on the carrier is from 0.1 to 20 percent by weight, though both higher and lower concentrations are possible. The concentration of tellurium and antimony, which may be regarded as auxiliaries, may also vary within wide limits, and is in general from 0.5 to 10 percent by weight.

In principle, carriers such as active charcoal, silica gel, silicic acid, alumina, clay, bauxite, magnesia, kieselguhr, pumice and the like may be used to manufacture the catalyst. The carriers may have been activated by conventional methods, eg. by treatment with acids. Active charcoal has proved a particularly advantageous carrier. The particle size of the catalyst is in general from 0.1 to 10 mm and depends, in the conventional way, on the particular arrangement used for the industrial operation of the process.

The butenediol diacetates which may be manufactured by the process of the invention are valuable intermediates for the manufacture of, eg., butane-1,4-diol, tetrahydrofuran and vitamin A. The invention is explained in more detail below by means of Examples which are explanatory only and do not limit the invention.

EXAMPLE 1

53.3 g of palladium chloride and 12.0 g of tellurium dioxide are dissolved in 4,000 ml of 6 N hydrochloric acid; 500 g of active charcoal (from 0.2 to 0.4 mm $\theta$), which have beforehand been extracted by boiling with 15 percent strength nitric acid, are added to the above solution and the mixture is slowly evaporated to dryness on a waterbath. After further drying, effected by passing a stream of nitrogen gas at 150° C. for 20 hours through the catalyst in a tube, the material is reduced by introducing a stream of nitrogen gas, saturated with methanol at room temperature, at a rate of 50 l/minute for 10 hours at 200° C. and then for 10 hours at 400° C.

0.5 l of the catalyst thus produced is filled (see FIGURE) into a pressure-resistant reaction tube 6, which is 4,000 mm long and has a diameter of 20 mm. Glass rings are introduced into the tube above the catalyst. Per hour, 0.75 l of liquid butadiene via 1a, 6 l of acetic acid via 1b and 20 l (S.T.P.) of oxygen via 4 are then introduced into the mixing apparatus 5 (a tube of size 4,000 × 6 mm, filled with metal spirals) at 30 bars and 90° C. A sight glass, not shown in the drawing, is provided above the mixing apparatus, to check whether the oxygen has dissolved completely.

The solution thus obtained is fed into the top of the reactor by means of the pressure from a pump 3. The reaction product discharged is fed into a separator 7, from where it is continuously withdrawn from the installation. (A part of the reaction product can, if appropriate, be recycled via the non-return valve 8.

Over a period of 148 hours, the space-time yield (g of diacetate/l of catalyst.hr) averages 250. The diacetate discharged contains 8.9% of but-1-ene-3,4-diol diacetate and 89.8% of but-2-ene-1,4-diol diacetate.

EXAMPLE 2

18.1 g of platinum chloride, 10.8 g of tellurium dioxide and 3.9 g of antimony chloride are dissolved in 4 l of 6 N hydrochloric acid, 0.75 l (340 g) of active charcoal (2 mm diameter) which has beforehand been extracted by boiling with 15 percent strength nitric acid, is added, and the mixture is slowly evaporated to dryness on a waterbath. After drying for 5 hours at 150° C., the catalyst is reduced, as in Example 1, for 19 hours at 200° C. and 40 hours at 400° C.

0.5 l of the catalyst thus produced is filled into the apparatus outlined in Example 1, and the reaction is carried out in the manner described above, at 95° C. and 30 bars, using 10.0 l/hour of acetic acid, 700 ml/hour of butadiene and 20 l (S.T.P.)/hour of oxygen. Over a period of 200 hours, the diacetates are obtained in an average space-time yield of 110 g/l.hr. The product contains 19.3% of but-1-ene-3,4-diol diacetate and 79.4% of but-2-ene-1,4-diol diacetate.

We claim:

1. In a liquid state process for the manufacture of but-2-ene-1,4-diol diacetate and/or but-1-ene-3,4-diol diacetate in which butadiene, oxygen and acetic acid are reacted in a reaction chamber over a solid catalyst which contains palladium and/or platinum as well as tellurium and/or antimony, the improvement which comprises: dissolving all of the gaseous reactant in the liquid reactant in a mixing apparatus separate from the reaction chamber and thereafter passing the reactants into a reaction chamber which is filled with liquid whereby the reaction takes place in the absence of a gas phase.

2. A process as set forth in claim 1, wherein a vertical tube reactor is used as the reaction chamber.

3. A process as set forth in claim 1, wherein an operating pressure of from 5 to 50 bars is maintained.

4. A process as set forth in claim 1, wherein the temperature is from 60° to 120° C.

5. A process as set forth in claim 1, wherein the catalyst used is a palladium catalyst or platinum catalyst on active charcoal as the carrier.

6. A process as set forth in claim 1, wherein the palladium and/or platinum catalyst is supported on a carrier, said catalyst being used in the amount of from 0.1 to 20% percent by weight.

7. A process as set forth in claim 6, wherein the amount of tellurium and/or antimony used in said palladium and/or platinum catalyst is from 0.5 to 10 percent by weight.

* * * * *